US006581472B2

(12) United States Patent
Schneider et al.

(10) Patent No.: US 6,581,472 B2
(45) Date of Patent: Jun. 24, 2003

(54) METHOD OF MONITORING AND CONTROLLING A SCREWING PROCESS

(75) Inventors: Eckhardt Schneider, Riegelsberg (DE); Rüdiger Herzer, Saarbrücken (DE)

(73) Assignee: Fraunhofer Gesellschaft zur Förderung der angewandten Forschung e.V., München (DE)

( * ) Notice: Subject to any disclaimer, the term of this patent is extended or adjusted under 35 U.S.C. 154(b) by 0 days.

(21) Appl. No.: 09/940,437

(22) Filed: Aug. 29, 2001

(65) Prior Publication Data
US 2002/0023503 A1 Feb. 28, 2002

(30) Foreign Application Priority Data

Aug. 29, 2000 (DE) .......................... 100 42 291

(51) Int. Cl.⁷ .......................... F16B 31/02; G01N 29/00
(52) U.S. Cl. .............................. 73/761; 73/597; 73/598
(58) Field of Search ..................... 73/761, 597, 598

(56) References Cited

U.S. PATENT DOCUMENTS

| | | | | |
|---|---|---|---|---|
| 3,969,810 A | | 7/1976 | Pagano | 73/581 |
| 4,294,122 A | * | 10/1981 | Couchman | 411/14 |
| 4,413,518 A | * | 11/1983 | Jones | 367/108 |
| 4,471,657 A | * | 9/1984 | Voris et al. | 73/597 |
| 4,530,143 A | * | 7/1985 | Casarcia | 29/407.02 |
| 4,601,207 A | * | 7/1986 | Steblay | 405/259.1 |
| 4,846,001 A | * | 7/1989 | Kibblewhite | 310/322 |
| 5,216,622 A | * | 6/1993 | Kibblewhite et al. | 700/275 |
| 5,675,087 A | * | 10/1997 | MacLauchlan et al. | 73/597 |
| 6,314,817 B1 | * | 11/2001 | Lindback | 73/761 |

* cited by examiner

Primary Examiner—Helen Kwok
Assistant Examiner—Rose M. Miller
(74) Attorney, Agent, or Firm—Breiner & Breiner, L.L.C.

(57) ABSTRACT

In the present method for monitoring and controlling a screwing process in creating a screw connection, ultrasonic pulses are coupled into the screw using a pulse-echo method before and during the tightening of the screw. The time for the pulses to traverse the length of the screw, i.e., the propagation time, is measured. A dependency of the propagation time on the predetermined tension of the screw is calculated from the material specific characteristic values of the screw and the measured propagation time. By comparing the values of a change in propagation time dependent on a parameter of the screw with the values of a change in propagation time dependent on the predetermined tension of the screw, the screwing process can be monitored.

9 Claims, 1 Drawing Sheet

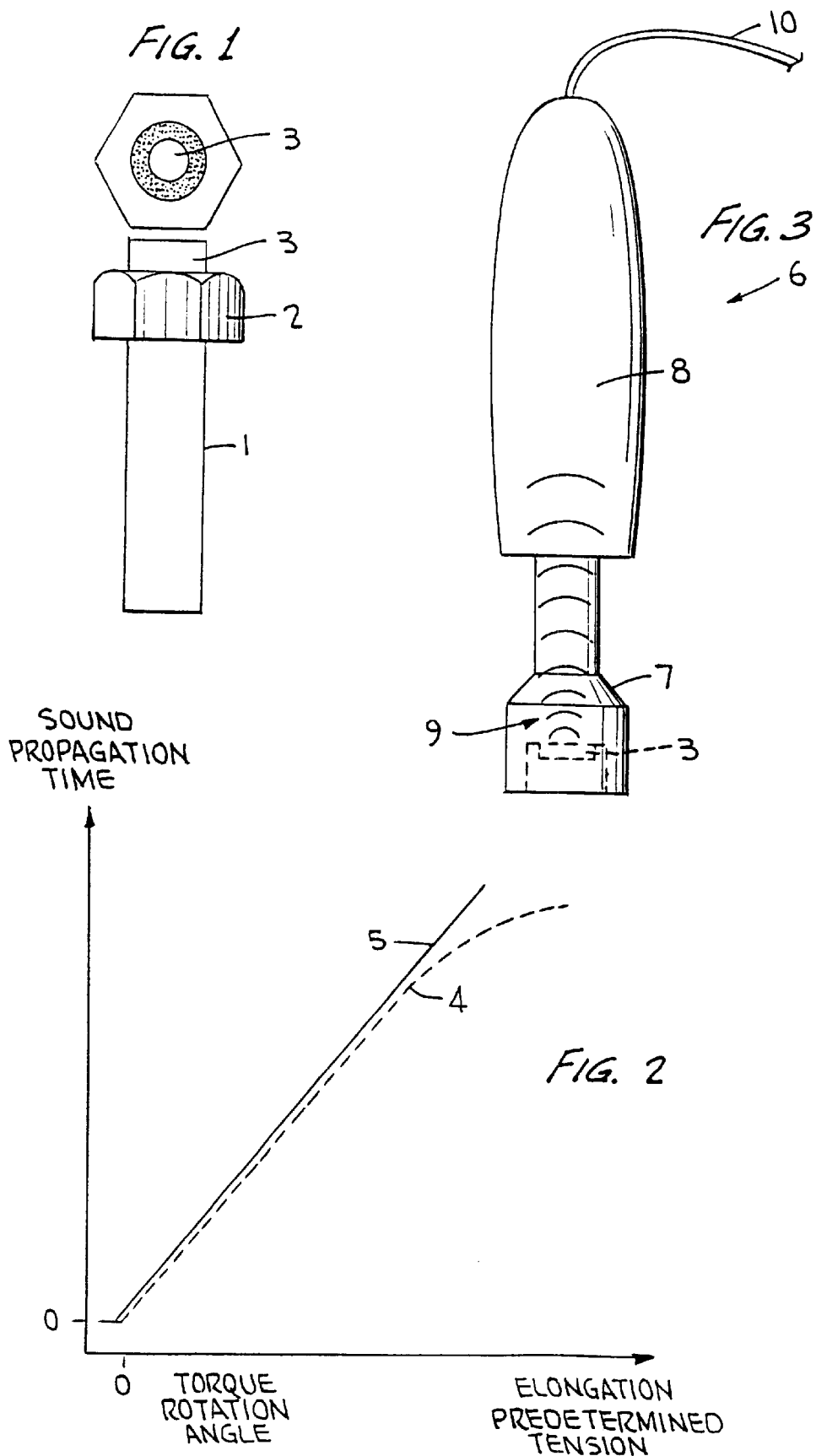

METHOD OF MONITORING AND CONTROLLING A SCREWING PROCESS

TECHNICAL FIELD OF APPLICATION

The present invention relates to a method of monitoring and, if needed be, of controlling a screwing process in the creation of a screw connection using a screw, wherein ultrasonic pulses are repeatedly coupled into the screw starting from the head of the screw using a pulse-echo method and the time (propagation time) it takes the ultrasonic pulses to traverse the length of the screw is measured.

The present method is particularly suited for automated screwing processes in industrial production in order to continually determine the predetermined tension force of the screw during the screwing process and to be able to control the screwing process accordingly.

STATE OF THE ART

Reliable achievement of a minimum predetermined tension force in a screw connection in serial assembly plays an essential role in the manufacture of many products. Poor predetermined tension force may result in the failure of heavy-duty screw connections with serious consequences. Due to additional influencing factors, such as friction losses, traditional methods with torque control and torque angle control for producing a screw connection, however, do not achieve the precision required for reliable setting of the predetermined tension force. For several years, ultrasonic methods of determining the predetermined tension force have been employed in addition to these indirect means of determining the predetermined tension force.

For example, Krautkrämer GmbH & Co. sells ultrasonic control devices which repeatedly couple ultrasonic pulses into the screw starting from the head of the screw using a pulse-echo method before and during the tightening process and measure the time it takes the ultrasonic pulses to traverse the length of the screw. Taking into account the acousto-elastic effect, screw elongation can be calculated from the time it takes the ultrasonic pulse to traverse the length of the screw and therefrom the, if desired, tension or the predetermined tension force. The systems known under the names Stress Mike® and Boltmike® store in a microcomputer system the calibration constants for determining the predetermined tension from the measured propagation times. The calibration has to be determined for the respective screw materials before conducting the screwing process using concrete measurements and then those have to programmed into the computer. In one embodiment of the mentioned systems, upper and lower predetermined tension force limit values, with an alarm signal sounding off when they are achieved, can also be entered.

In both systems, a separate measuring probe is mounted on the head of the screw via which the ultrasonic pulse can be coupled in and the reflected signals can be received.

In order to improve sound propagation and reflection relationships, the surfaces of the screw head and screw end are designed by the screw manufacturer according to various optimization concepts. Thus, for example, it is known to apply a piezoelectric layer on each screw head during screw production. The ultrasonic pulses can then be generated in a simple manner via this piezoelectric layer simply by means of suited electric activation and the reflected signals can be received again. This facilitates, in particular, application of known ultrasonic methods in rotating screw tools, as is realized in Ultrafast®'s control systems.

Despite many attempts to improve the methods of determining the predetermined tension force of screws, hitherto such type systems have proven unsatisfactory in regard to measuring precision and reliability in serial production, particularly in automobile production. Especially the required precision and reliability have hitherto not fulfilled expectations.

DE 42 31 429 C1 describes a screwing process in which monitoring the tightening process is conducted using an ultrasonic measuring process. The ultrasonic pulses are repeatedly coupled into the screw starting from the head of the screw using a pulse-echo method before and during the tightening process and the time it takes the ultrasonic pulses to traverse the length of the screw are measured (propagation time). In order to begin the screwing process, a first propagation time measurement is conducted on the load-free screw and the measured value is stored. During the screwing-in process respectively the tightening process, further propagation time measurements are conducted with a high rate of repetition. The detected changes in the propagation time are compared with reference values the propagation time change, which were previously recorded in a table. These table reference values were previously determined empirically. When a change in the propagation time corresponds to a desired predetermined tension in the table is achieved, tightening is discontinued.

Based on this state of the art, the object of the present invention is to provide a further method of monitoring and, if need be, of controlling a screwing process in the creation of a screw connection using a screw which provides great reliability and precision and, in particular, permits detection of any significant deviation from the prescribed specifications of the used screw.

DESCRIPTION OF THE INVENTION

In the present method ultrasonic pulses are repeatedly coupled into the screw starting from the head of the screw using a pulse-echo method before and during the tightening process and the time it takes the ultrasonic pulses to traverse the length of the screw is measured. It is fundamentally sufficient to measure the value of the sound propagation time of the load-free screw once before starting to tighten, for example already during screwing in of the screw. However, repeated measuring increases measuring precision.

Furthermore, prior to starting to tighten the screw, the change in sound propagation time is calculated from the material-specific characteristic values of the screw and from the once or repeatedly measured values of the sound propagation time in the load-free screws before tightening the screw as a function of the tension in the screw respectively the predetermined tension of the screw is calculated and stored. This calculation is based on the known material-specific constants of the type of screw employed. From the sound propagation time values repeatedly measured during tightening of the screw, at least one value is determined for the relationship between the change in the propagation time and the change in a screw parameter which influences the predetermined tension of the screw. This screw parameter may be, for example, the torque, the torque angle or the screwing-in time with a constant torque. Finally during tightening of the screw, the value or values for the relationship between the stored dependency of the changes in propagation time and the change in predetermined tension determined from the propagation time measurements are compared.

This comparison of the rise of a calculated theoretic curve of the type of screw used with the values measured during tightening of the screw permits drawing a conclusion as to whether the actually employed screw meets the specifications. Furthermore, this comparison permits drawing conclusions as to whether the selected screw parameters have been correctly selected for carrying out the current screw process. Thus, the comparison can, in particular, be utilized to influence the respective screw parameter in the event of a deviation from the values determined from measuring the propagation time from the stored values in order to minimize the deviation. A deviation, lying significantly above or below the prescribed value, of the value determined from the propagation time measurements from a stored value is preferably indicated so that, if need be, the screwing process is discontinued manually or automatically. Such a significant deviation is a sign that the specifications of the used screw do not meet the prescribed specifications. Furthermore, in such an event there may be unanticipated secondary conditions for screwing which may negatively influence the screwing result. Keeping in mind the desired high degree of reliability, in both instances, it is necessary to discontinue the screwing process.

A comparison of the calculated and the measured data permits readily determining the time when the prescribed desired predetermined tension of the screw has been achieved. Based on the stored values, the desired propagation time can be calculated from the desired predetermined tension so that the screwing process can be stopped if the measured propagation times correspond to this desired propagation time. If the time intervals of the individual measurements are constant, the change in propagation times until the next measurement or the time until the desired propagation time is achieved can also be predicted.

In realizing the present invention, the inventors recognized that the unsatisfactory results with the hitherto known methods are partly due to the fact that the properties of the screws used in practice distinctly differ from the those employed for calibration and therefore may significantly decrease the reliability of the implemented control. In the present method, particularly, the calculation of the changes in propagation time of the acoustic pulses in dependence on the predetermined tension based on the material specific characteristic values of the utilized type of screw makes the present method independent of the calibration measurements of a single screw. Deviations of the actually employed screw from the calculated data are detected in time so that malfunction is practically ruled out.

In the case of a significant deviation of the measured values from the calculated theoretic values, the screwing process is preferably discontinued in a first interval of tightening the screw, whereas no or only a minor deviation permits concluding that a correct screw has been employed and that the anticipated secondary conditions are present. In such a case, if there is a deviation of the values, only the screw parameters are changed accordingly in a second interval of the tightening process in order to minimize the calculated curve and achieve precisely the desired predetermined tension.

Due to the mentioned monitoring, the present process affords greater precision and reliability with which the required predetermined tension force can be achieved in the screwing process, thereby permitting better utilization of the tensile strength of the screw and obviating overdimensioning the screw for safety reasons.

The relationships for calculating the change in propagation time as a function of the predetermined tension force $\sigma$ from the material specific characteristic values of the screw on which the present method is based are given by the following equation:

$$(t_\sigma - t_0)/t_0 = \sigma(A/C).$$

With $t_0$ standing for the propagation time measured in the load-free screw during screwing in and $t_\sigma$ standing for the propagation time in the load-applied screw during the tightening process. A and C are a combination of material specific elastic constants of the $2^{nd}$ order ($\lambda$, $\mu$) and the $3^{rd}$ order (l, m, n) determined in the preliminary tests respectively have already been determined for many screw qualities. In this case, the following relationships apply:

$$A = 2(\lambda + \mu)(4m + 5\lambda + 10\mu + 2l) - 2\lambda(2l + \lambda)$$

$$C = -4\mu(\lambda + 2\mu)(3\lambda + 2\mu).$$

The constants $\lambda$ and $\mu$ are the material specific Lamé's constants which describe the elastic constants shear modulus and elasticity modulus. The constants l, m, and n are known to someone skilled in the art under the term Murnaghan constants.

In an embodiment of the present method, in which non-linear tension-expansion relationships dependent on the tensile strength class and the method of production of the screw are determined in preliminary tests and the obtained characteristic values are used for calculating the sound propagation time as the function of the predetermined tension of elongation screws tightened beyond the elastic limit, the above relationships have to be extended in such a manner that the change in sound propagation time can be calculated theoretically even if the screw is tightened beyond its elastic limits. In this event, the above equation is extended by adding an additional term with modified elastic constants and a square root tension term.

In the present method, the propagation time measurements during the tightening process are preferably conducted at least 100 times per second. Recording measured data recording of 200 and more single propagation time measurements per second in which the propagation time can be measured with a relative precision of better than 0.01% has proven to be especially advantageous. A suited measuring method is described, for example in DE 39 05 956.

Coupling the ultrasonic pulses into the screw can occur in a conventional manner via a specially designed drive means nut having an ultrasonic probe (as shown in FIG. 3) or via an also known from the state of the art electric activation of screws having a piezoelectric layer applied to them. The presently available coupling methods and coupling media for transmitting ultrasonic pulses from the probe into the screw and back ensure sufficiently constant sound input even if using conventional ultrasonic probes. Further developments in signal transmission technology permit, in particular, contactless signal transmission into respectively from rotating components. In the present method, as shown in FIG. 3 preferably such contactless signal transmission between the ultrasonic probe in the rotating element and the stationary element of the drive means nut is employed. Transmission to a data processing device for evaluation and comparison of the measured data can occur in a conventional manner via cables. The data processing device contains, in particular, a programmable microprocessor which controls the recording of the measured data and permits online comparison of the measured propagation time values with the previously calculated changes in the measured values which were calculated from the acousto-elastic characteristic values of the to-be-processed screws and stored in a memory.

BRIEF DESCRIPTION OF THE DRAWINGS

The present invention process is briefly explained once more in the following using a preferred embodiment with reference to the accompanying drawings without the intention of limiting the scope or spirit of the overall inventive idea.

FIG. 1 shows a lateral view and a top view of a screw having an ultrasonic probe mounted on it; and FIG. 2 shows an example of the dependency of the ultrasonic propagation time through the screw on the torque or torque angle or predetermined tension or elongation.

WAYS TO CARRY OUT THE INVENTION

FIG. 3 shows an embodiment wherein the coupling is by ultrasonic probe and the tightening process includes a drive means spindle with a rotating element and a stationary element, wherein the transmission of electric signals to and from the probe is in a contactless manner between the rotating element and the stationary element.

FIG. 1 shows a lateral and a top view of a screw 1 having a screw head 2 on which an ultrasonic transmitter and ultrasonic receiver 3 are mounted for coupling in ultrasonic pulses in the longitudinal direction of the screw and for receiving the signals reflected at the end of the screw. Such an ultrasonic transmitter is preferably integrated in the drive means nut of the corresponding screw driving tool (as shown in FIG. 3). The various possible means of triggering this probe and the conveyance of the data are familiar to someone skilled in the art and play no role in the present invention.

A conventional ultrasonic longitudinal wave probe, which transmits and receives the ultrasonic waves with a repeated frequency of approximately 1 kHz is employed for the process accompanying determination of the predetermined tension force during screwing in such a type screw. As soon as probe 3 is in mechanical contact with screw head 2, as depicted schematically in FIG. 1, the time it takes the ultrasonic pulse to traverse the length of the screw twice is measured. A microprocessor, not depicted in the figure, to which the measured data are transmitted calculates the mean value $t_0$ of the sound propagation time from a parameterizable number of single measurements. These measurements can occur during the screwing-in process of the screw, before starting the tightening process. In the event of multiple single measurements, the magnitude of the deviation from the norm can be used to control the sound input and sound signal shape to indicate poor coupling.

After the screwing-in phase of screw 1, the ultrasonic propagation time t increases as a result of the elongation caused by the tensile stress in the screw. FIG. 2 shows this relationship with the determined theoretic curve 5 which was previously calculated using the material specific, acousto-elastic characteristic values of screw 1 and stored in the microprocessor. This curve 5 shows the linear relationship between increase in elongation and increase in tension in the screw and the increase in propagation time very well.

Furthermore, the figure shows the dependency of the measured propagation times as a function (curve 4) of a screw parameter (here: the torque or the torque angle). From the parameterizable number of single measurements of the propagation time t as a function of the torque or another process parameter, for example the torque angle, the best straight line is calculated and its rise is compared with the rise of the calculated curve 5 stored in the computer. A significant deviation calls attention to irregularities. Such deviations can, for example, be caused by increased friction losses, in particular due to thread damage and/or due to a screw tensile strength that deviates from the prescribed tensile strength.

The propagation time $t_o$ which corresponds to the desired predetermined tension force is calculated from the predetermined tension force required or prescribed for the individual screw, the material specific characteristic values and the propagation time $t_0$ of the ultrasonic pulses in the load-free screw. As soon as the measured propagation time t reaches the propagation time value $t_o$ predetermined for the individual screw connection, the engine of the drive means is turned off.

In the region of the limit of elasticity, the measured propagation time curve deviates more or less strongly from the calculated ideal linear-elastic straight line. This can be seen in FIG. 2 with increasing tension. Dependent on the type of production and the tensile strength of the screw, this deviation from the linear course can also be directed upward, i.e. to longer propagation times. This material specific change can be determined experimentally for screws of different types of production and classes of tensile strength in previous tests so that the predetermined tension force can be determined from the deviation of the measured change from the calculated linear-elastic straight line even for screws that were drawn into the region of the limit of elasticity (beyond the elastic limit stress).

FIG. 3 illustrates an embodiment of the coupling and tightening process of the method of the invention. In particular, FIG. 3 shows coupling by the ultrasonic probe 3 and the tightening process by a drive means spindle 6 including a rotating element 7 and a stationary element 8. The transmission of electric signals 9 to and from the ultrasonic probe 3 occur in a contactless manner between the rotating element 7 and the stationary element 8. A conventional cable 10 is utilized for transmission to a data processing device as described above.

Reference Numbers 1 screw
2 screw head
3 ultrasonic transmitter probe respectively ultrasonic receiver probe
4 measured propagation time data
5 calculated theoretic propagation time data

What is claimed is:

1. A method for monitoring a screwing process in creating a screw connection with a screw, comprising:

(a) before starting a tightening process of said screw,
coupling at least one first ultrasonic pulse into said screw using a pulse-echo method, starting from a head of said screw, and measuring propagation time of said at least one first ultrasonic pulse for traversal of length of said screw;
calculating at least one value of a change in propagation time of said at least one first ultrasonic pulse as a function of a predetermined tension of said screw, the calculating being of material specific characteristic values of said screw and said propagation time; and
storing the at least one value for the change in propagation time as a function of said predetermined tension to provide stored values;

(b) during said tightening process,
repeatedly coupling second ultrasonic pulses into said screw using a pulse-echo method, starting from the head of said screw, and measuring propagation times of said second ultrasonic pulses for traversal of the length of said screw;

determining at least once a first value of a relationship between a change in propagation time and a change in a screw parameter influencing said predetermined tension of said screw from the propagation times measured of said second ultrasonic pulses;

determining at least one second value of the relationship between a change in propagation time and a change in said predetermined tension of said screw from said stored values; and comparing said at least one first value with said at least one second value.

2. A method according to claim 1, further comprising influencing said screw parameter to achieve a required predetermined tension in a prescribed process time when deviation of said at least one first value from said at least one second value occurs.

3. A method according to claim 1 or 2, wherein said method indicates a deviation above or below a prescribed value of said at least one first value from said at least one second value.

4. A method according to claim 1 or 2, further comprising discontinuing said tightening process when deviation above or below a prescribed value of said at least one first value from said at least one second value occurs.

5. A method according to claim 1 or 2, further comprising before starting the tightening process, calculating a desired propagation time from a prescribed tension of the screw, said material specific characteristic values of said screw and said propagation time measured; said propagation time measured being compared with said desired propagation time and upon achieving said desired propagation time, discontinuing said tightening process.

6. A method according to claim 1 or 2, further comprising determining said material specific characteristic values in preliminary tests, said material specific values being dependent on tensile strength class and method of production of said screw.

7. A method according to claim 1 or 2, further comprising determining a material specific non-linear tension-elongation relationship dependent on tensile strength class and method of production of said screw in preliminary tests, and obtaining characteristic values for calculating sound propagation time as a function of predetermined tension of stretch screws tightened beyond their elastic limit.

8. A method according to claim 1, wherein said measuring of said propagation time occurs at least 100 times per second.

9. A method according to claim 1, wherein said coupling is by an ultrasonic probe and said tightening process is by a drive means spindle having a rotating element and a stationary element, and transmission of electric signals to and from said ultrasonic probe occur in a contactless manner between said rotating element and said stationary element.

* * * * *